United States Patent [19]

Margraf

[11] 3,932,627

[45] Jan. 13, 1976

[54] SIVER-HEPARIN-ALLANTOIN COMPLEX

[75] Inventor: Harry W. Margraf, Clayton, Mo.

[73] Assignee: Rescue Products, Inc., Bridgeton, Mo.

[22] Filed: Feb. 4, 1974

[21] Appl. No.: 439,314

[52] U.S. Cl............... 424/183; 260/211 R; 424/245
[51] Int. Cl.² ................. A61K 31/725; C08B 37/10
[58] Field of Search.......... 424/183, 245; 260/211 R

[56]         References Cited
          UNITED STATES PATENTS

| | | | |
|---|---|---|---|
| 2,336,131 | 12/1943 | Schaffer | 260/299 |
| 3,549,409 | 12/1970 | Dyck | 424/183 |
| 3,673,612 | 7/1972 | Merrill et al. | 424/183 |

*Primary Examiner*—Sam Rosen
*Attorney, Agent, or Firm*—Michael Kovac

[57]         ABSTRACT

Silver-heparin-allantoin complex and process for making same is disclosed. The silver-heparin-allantoin complex is prepared by a novel process in either powder or solution form. The silver-heparin-allantoin complex provides a non-thrombogenic, self-sterilizing compound for application to polymeric devices such as prosthetic values, small diameter arterial grafts and the like to avoid thrombus formation and infection of polymeric devices.

3 Claims, No Drawings

SIVER-HEPARIN-ALLANTOIN COMPLEX

BACKGROUND OF THE INVENTION

A wide variety of materials have been developed and studied in the search for synthetic replacements for vital internal body parts. Specific study has been focused on prosthetic implant devices used in vascular and cardiac surgery where there is a present need to replace defective or diseased valves and arteries. From this research will come further developments of synthetic replacement devices for other vital body parts.

While flexible, life-like polymeric materials are the most promising for certain internal organs, there are serious problems stemming from the reaction of blood on the polymeric surfaces. This may cause the rupture of red cells and the escape of hemoglobin into the plasma, a condition known as hemolysis, or initiate complex biochemical reactions that lead to thrombosis or clotting.

All polymeric devices, even the so-called non-thrombogenic polymers such as silicone rubber, cause blood clotting in a short period of time. Polytetrafluoroethylene, tetrafluoroethylene, and other polymeric substances are similarly deficient. Whether the polymeric devices are implanted into the body as heart valves, aortas or blood vessels are used as tubing in heart-lung or kidney machines, the blood from the body comes into direct contact with polymers.

It was not until plastic surfaces were treated with heparin, a sulfated mucopolysaccharide found in human lung tissue, blood vessel walls, the liver and small amounts of blood, that the resulting plastics became non-thrombogenic. Several techniques have been developed for chemically binding heparin to surfaces of prosthetic devices. The result has been that heparin-coated polymeric materials effectively retard blood clotting, as shown from both in vitro and in vivo studies, and promise increased use of polymeric devices for use with the body, whether directly implanted or as part of life-generating machine systems.

Equally as serious as the problem of thrombus formation on the prosthetic material is the problem of infection of the prosthetic implant. Prosthetic heart valves and tubular graft materials have displayed vegetative overgrowth caused by bacteria and fungi. These organisms are likely to cover the skirt and strut of the ball and cage type valves as well as the entire surface of the tubular grafts. Infection of the prosthetic implant can lead to disastrous complications including remedial surgery to replace the infected prosthetic implant. What has been needed; therefore, is a non-thrombogenic and anti-microbial composition for application to polymeric devices for use with the body.

SUMMARY OF THE INVENTION

A principal object of the present invention is to treat polymeric devices to be used in contact with the human body with a protective antimicrobial and thromboresistant coating.

A further object of the present invention is to develop a stable anti-microbial and non-thrombogenic composition which can be chemically or electrostatically bound to polymeric devices.

Still another object of the present invention is to provide a method of preparing a composition which serves the foregoing objects.

It has been discovered that when ammonium heparinate is appropriately treated with a compound such as silver allantoinate or physiological salt derivatives of same, complexes are readily formed which may be isolated in the form of white crystalline powders or utilized in solution form. In either case, the anti-coagulant properties of heparin and the anti-microbial properties of silver can be usefully employed for polymeric devices used in contact with the body.

DESCRIPTION OF THE INVENTION

The silver-heparin-allantoin complex, also referred to herein as silver-heparin-allantoinate, is prepared as more fully set forth below by reacting ammonium heparinate with ammonium allantoinate and silver allantoin. The resulting complex consists of silver-heparin-allantoinate. The complex combines the anti-microbial properties of silver with the anti-coagulant properties of heparin and the amphoteric complexing ability of allantoin to form a lasting coating or impregnation of polymeric devices used with the body.

Silver is employed for its anti-microbial characteristics which inhibit the growth of bacteria and prevent bacteria invasion. It has been known for several centuries that various forms of silver, including the pure metal, certain of its derivatives and colloidal suspensions have antiseptic or germicidal characteristics. The bactericidal power of metallic silver has what has been termed oligodynamic activity to describe the lethal properties of any metal exhibiting anti-microbial properties in small concentrations. In addition to the antiseptic characteristics of metallic silver, it is also non-toxic.

Silver has also been used in the form of various salts for bactericidal purposes. Some of the silver salts include silver nitrate, silver citrate, silver lactate, silver picrate, silver chloride, silver proteinate and many others. The practical value of such silver salts has been restricted due to the irritating, astringent, caustic and sometimes toxic ion complexed with silver such as the toxicity of the nitrate ion in silver nitrate. There are other known disadvantages of such silver salts including the loss of efficiency of the silver due to reaction of the silver ions with and absorption into body tissues, body fluids and dressings.

From U.S. Pat. No. 2,336,131, it is known that silver allantoinate avoids the irritating and erosive effects of silver nitrate and offers the healing qualities of allantoin. Allantoin is a nitrogenous crystalline substance that has known healing and debriding qualities. What is not generally known about silver allantoin is that ionic silver is made available by a slow, progressive release process. This results since allantoin is an amphoteric substance (contains positive and negative charges to form salts and complexes) which readily combines with silver to slowly release free silver ions and provides a highly effective antimicrobial action. In my patent application Ser. No. 167,737, filed July 23, 1971 now U.S. Pat. No. 3,830,824, I have disclosed that a physiological organic acid silver allantoinate is preferable because it incorporates acids occurring or taking part in normal metabolic processes which avoid chemical reactions that might be harmful or irritating.

I have also disclosed in Ser. No. 153,820 filed June 16, 1971 now U.S. Pat. No. 3,856,805, that is silver-zinc-allantoinate complex may be formed to provide a stable compound with anti-bacterial and anti-fungal properties, while in Ser. No. 165,753 filed July 23, 1971 now U.S. Pat. No. 3,830,908, I have disclosed an anti-microbial composition utilizing a physiologically compatible organic acid silver salt allantoin complex and a zinc sulf-hydroxy allantoinate which also provides anti-bacterial and anti-fungal qualities. The zinc sulf-hydroxy allantoinate complex is disclosed in Ser. No. 165,736 filed July 23, 1971, now U.S. Pat. No. 3,830,825

The heparin derivative of the silver-haparin-allantoin complex is designed to react with functional groups on the polymeric surfaces, i.e. with reactive amine (—NH) groups. As has been discussed above, heparin-coated polymeric materials effectively retard blood clotting of prosthetic implants to make them non-thrombogenic.

To reduce the infection problem of prosthetic implants and to promote healing of adjacent tissues, it was discovered that a stable silver-heparin-allantoin complex could be formed which would also have free valences to form co-valent bonds with active groups on polymeric materials. The relative insolubility of the silver-allantoin derivatives in the complex of the present invention required the use of a suitable solvent. Among the alkalis tested, ammonium hydroxide worked quite well, although it is conceivable that other alkaline solubulizers may be suitable for the preparation of the silver-heparin-allantoin complex in solution for purposes of surface coating or impregnation on polymeric materials.

It has thus been discovered that when ammonium heparinate is appropriately treated with a compound such as silver allantoinate or physiological salt derivatives of same, complexes are readily formed in either powder or solution form to produce the anti-coagulant properties of heparin with the anti-microbial properties of silver and the amphoteric complexing ability of allantoin for surface coating or impregnation of polymeric devises to be used with the human body.

The silver-heparin-allantoin complex is prepared by the process set forth in the following example:

EXAMPLE NO. 1

The following primary solutions must first be prepared in order to prepare a solution of the silver-heparin-allantoin complex:

1. Ammonium heparinate is distilled water: Commercially available powder is dissolved in distilled water using 2 grams per 100 ml of distilled water. This approximates 200,000 units of heparin per 100 ml of solution.

2. Ammonium Allantoinate: 40 grams of allantoin, C.P. are dissolved in 1000 ml of distilled water containing 35 ml of ammonium hydroxide, 58%.

3. Silver Allantoin (preferably silver-citro-allantoinate): 13 grams of silver allantoin are dissolved in 100 ml of solution 2. This results in silver concentration approximating 4% ionic silver and complexed silver.

These solutions are quite stable if individually stored (preferably in cool, dark places). If it is desired to vary the eventual silver and heparin content of the "treatment" solution described below, the concentrations of the ingredients of the above solutions may be altered, as may be desired.

An example of a "treatment" solution to immerse polymeric devices for coating or impregnation is as follows (to be mixed in the order listed):

|  |  | Or |
|---|---|---|
| Solution 1 (Ammonium heparinate) - | 100 parts | 100 parts |
| Solution 3 (Silver solution) - | 100 parts | 100 parts |
| Solution 2 (Ammonium allantoinate) - | 100 parts | 295 parts |
| Hydrogen peroxide, 3% - | 5 parts | 5 parts |
| Freshly distilled water - | 195 parts | — |

The resulting solution has a PH (hydrogen ion concentration) of 9 and contains approximately 0.8% silver, 2.8% allantoin and 40,000 units of heparin per 100 ml.

Precipitation of the silver-heparin-allantoin complex is easily attained by removal of free ammonia and cooling. The precipitate consists of a white, crystalline powder which may be re-dissolved in dilute alkali, such as ammonia, or which may be isolated and handled in dry form for whatever uses contemplated.

In order to coat or impregnate polymeric materials, it has been found that the best results are achieved if the polymeric materials are treated first by immersion into a mixture of acetone:methanol, 50:50 V/V, for approximately 15 minutes to establish a more reactive surface free from organic contamination. This is followed by rinsing with distilled water and complete immersion into the "treatment" solution. Maximal coating or impregnation of polymeric materials has experimentally been determined by a minimum immersion of 60 minutes at a temperature of 37°C. Longer immersion times permits deeper penetration of the silver-heparin-allantoin complex which is usually not needed and is wasteful.

The treated polymeric material is then rinsed with distilled water and air dried, or first air dried, rinsed with distilled water and again air dried. It should be stored protected from direct sunlight, preferably at room temperature, and it can be gas-sterilized before use.

Silver-citro-allantoinate is preferred in preparing the silver-heparin-allantoin complex because of the anticoagulant properties of the salts of citric acid, i.e. sodium citrate. The use of hydrogen peroxide in the treatment solution prevents limited reduction of the ionic silver by prophylactically inhibiting reduction and the resultant discoloration. It also prolongs shelf life of the powder or solution. Hydrogen peroxide, benzoyl peroxide or other suitable oxidants would also be effective in other silver salt compounds.

The anti-microbial and anti-thrombogenic properties of polymeric materials thus coated or impregnated have been tested, both in vitro and in vivo. Commercially available Dacron knitted and velour 12 mm diameter polyester protheses were treated with a variety of chemical solutions and gas sterilized. Untreated portions from the same prosthesis served as controls. Bacterial growth of 4 organisms in the presence of the prostheses was tested. Thromboresistance studies consisted of superior vena cava replacement in 63 dogs and angiography in all survivors at 4–8 weeks and 27 at 6–8 mos. Eleven dogs had 50,000 *Staph Aureus* injected at the graft site 6 weeks postoperatively and the prostheses recovered 7 days later. All dogs were autopsied and the changes in anatomic and mid-lumenal diameters, thickness and characteristics of the inner and outer capsules and graft stiffness were recorded. The results show that of the five chemical processes used, the two silver-heparin-allantoin treatments yielded the highest patency rate (21/23 or 91%) vs. controls (10/15 or 67%) for nonvelour grafts. The velour prosthesis had a low patency rate (33%) regardless of chemical treatment. No bacterial growth was found with Silver-heparin-allantoin complex treated prosthesis vs. florid growth in the control prosthesis cultures. After bacteremia, the control grafts yielded greater than 7,000 fold more bacteria than the silver-heparin-allantoin complex treated grafts. These grafts had the greatest compliance and thinnest outer and inner capsules 6–8 mos. after implantation. It was concluded from the tests that silver-heparin-allantoin complex treatment of commercial Dacron vascular prostheses results in: (1) a bacteriostatic surface which is active at least 7 weeks after graft implantation, (2) improved thromboresistance, and (3) favorable modification of the long term tissue response to the prostheses.

From the foregoing, it will now be apparent that the present invention discloses a non-thrombogenic and anti-microbial composition for treatment of polymeric devices and a method of preparing same.

I claim:

1. A non-thrombogenic and anti-microbial complex for application to body contact polymeric devices consisting essentially of silver-heparin-allantoinate.

2. The composition of claim 1 in which the silver-heparin-allantionate is present in solution in an amount of 60 ml per 100 ml of solution.

3. The composition of claim 2 in which silver is present in the amount by weight of 0.8%, allantoinate is present in the amount of 2.8%, and there are approximately 40,000 units of heparin in each 100 ml of solution.

* * * * *